United States Patent
Meyer (10) Patent No.: US 9,452,251 B2
(45) Date of Patent: Sep. 27, 2016

(54) DEGASSING MEMBRANE FOR DIALYSIS (71) Applicant: Medtronic, Inc., Minneapolis, MN (US)

(72) Inventor: Thomas E. Meyer, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/566,692

(22) Filed: Dec. 10, 2014

(65) Prior Publication Data

US 2016/0166752 A1 Jun. 16, 2016

(51) Int. Cl.
*B01D 19/00* (2006.01)
*A61M 1/16* (2006.01)

(52) U.S. Cl.
CPC ........ *A61M 1/1658* (2013.01); *B01D 19/0031* (2013.01); *B01D 19/0063* (2013.01); *B01D 19/0073* (2013.01)

(58) Field of Classification Search
CPC .......... B01D 19/0031; B01D 19/0063; B01D 19/0073; B01D 61/24; B01D 71/70; A61M 1/16; A61M 1/1658; A61M 1/3627
USPC ..................................................... 95/46; 96/6
See application file for complete search history.

(56) References Cited

U.S. PATENT DOCUMENTS

| | | | | |
|---|---|---|---|---|
| 3,631,654 A * | 1/1972 | Riely | ................ | B01D 19/0031 96/6 |
| 4,325,715 A * | 4/1982 | Bowman | ............ | B01D 19/0031 95/6 |
| 5,194,158 A * | 3/1993 | Matson | ............. | B01D 19/0031 95/46 |
| 6,248,157 B1 * | 6/2001 | Sims | ................. | B01D 19/0031 95/46 |
| 6,316,684 B1 * | 11/2001 | Pinnau | .................. | B01D 69/02 210/500.21 |
| 7,947,112 B1 * | 5/2011 | Gerner | ............... | B01D 19/0063 95/46 |
| 2003/0234030 A1 * | 12/2003 | Shibayama | ........ | B01D 19/0031 134/2 |
| 2008/0014622 A1 * | 1/2008 | Federspiel | ............. | B01D 71/70 435/182 |
| 2011/0087187 A1 * | 4/2011 | Beck | .................. | B01D 19/0031 95/46 |
| 2014/0112828 A1 * | 4/2014 | Grant | .................. | A61M 1/1658 422/44 |

* cited by examiner

*Primary Examiner* — Jason M Greene
(74) *Attorney, Agent, or Firm* — Hahn & Associates PLLC; Roger C. Hahn; Kenneth J. Collier (57) ABSTRACT

The degasser can have a degassing membrane that can be constructed from non-porous silica. The degassing membrane can be highly permeable to carbon dioxide but less permeable oxygen or nitrogen gases. Pressure in the dialysate and the degasser can be controlled in order to control the amount of carbon dioxide and other gases in dialysate leaving the degasser. The degassing membrane may be placed in a degassing module in a dialysate flow path to remove dissolved carbon dioxide from the dialysate.

22 Claims, 6 Drawing Sheets

DEGASSING MEMBRANE FOR DIALYSIS

FIELD OF THE INVENTION

The invention relates to a degassing system having a membrane for degassing fluids during dialysis and methods for using such a system and related methods.

BACKGROUND

Dialysis involves the movement of blood through a dialyzer having a semi-permeable membrane. The water supply used to initially prepare the dialysate or used during or after dialysis may contain a significant amount of dissolved gas such as nitrogen, oxygen, or carbon dioxide. Carbon dioxide may be formed as part of the breakdown of urea as spent dialysate flows through the sorbent cartridge. Removal of dissolved and undissolved gases from dialysate in a dialysis system can be important because dissolved gases can come out of solution in the dialysate circuit and cause gas bubbles, which can interfere with the proper functioning of the dialysis system. Gas bubbles can interfere with the smooth pumping of the dialysate in the dialysate loop, interfere with sensors in the dialysate loop, and can present a dangerous condition for the patient if the gas bubbles cross the dialyzer membrane into the patient's blood stream, potentially causing an air embolism.

Several methods and apparatuses are known in the art for degassing dialysate. For example, a pressure regulating system for a hemodialysis machine utilizes a deaeration pump and a regulator in a deaeration loop for minimizing pressure and flow transients in a heated water supply. The deaeration loop comprises a pump, a deaeration pressure regulator, a deaerator, and a back pressure regulator. The pump produces a negative pressure in heated water entering the deaeration pressure regulator to circulate the water in the deaeration loop and to enhance removal of air from the water. The back pressure regulator controls the loop water pressure to a value less than the incoming water pressure and supplies water to the dialyzer system of the machine isolated from supply water pressure and flow variations.

In an artificial kidney, dialysate concentrates and heated water are fed separately by pumps in fixed proportions to a mixing venturi where the water and liquid are combined to form a dialysate solution. In order to remove from the dialysate solution a desired portion of air which has been introduced therein from the water, the heated water is passed through a positive displacement pump having a restricted orifice bypass line before the heated water arrives at the mixing venturi. This causes consolidation of the air from small to large bubbles which are removed by a bubble trap. The resulting deaerated solution is then advanced through a header to branch lines to dialyzers.

A known apparatus for exposing a fluid to a negative pressure, particularly for degassing liquid containing a gas, comprises a double acting piston/cylinder unit of which the cylinder is divided into two chambers by the piston, the volume of one chamber swept by the piston being lesser than that swept by the piston in the other chamber. An inlet for a fluid is made to said one chamber, a conduit connects the two chambers and an outlet is made from the other chamber. Valve means are associated with the conduits to permit controlled reciprocation of the piston within the cylinder and fluid passed from said one chamber to the other is exposed to a negative pressure in the other chamber. In the situation in which the fluid is a gas-containing liquid, this negative pressure results in the formation of bubbles in the other chamber; alternatively, where the fluid is wholly liquid, a part of that liquid is vaporized. The contents of the other chamber are then passed through the outlet from the other chamber to, where the fluid is a gas-containing liquid, a bubble trap in which the gas is separated from the liquid or, where the fluid is wholly liquid, the gaseous phase or vapor will be condensed upon release of pressure and moved through the outlet to be used as required. In a variation, the piston/cylinder structure is replaced by a simple receptacle provided with a flexible diaphragm.

The known systems and methods cannot actively control a degassing process in order to selectively control a specific dissolved gas concentration within a desired range Instead, the systems described allow for general air removal from dialysate.

Hence, there is a need for a degassing system that can remove unwanted dissolved and undissolved gases from fluid before, during and after dialysis therapy. There is a need for a degassing system having the small size and weight necessary for a portable dialysis system. There is also a need for a degassing membrane that can allow a high degree of control over specific gas levels in dialysate. There is further a need for a degassing device that can function to remove specific gases with particularity from closed circuit dialysis systems.

SUMMARY OF THE INVENTION

The first aspect of the invention is directed to a degassing system having a membrane to be used for degassing dialysate during dialysis. In any embodiment of the first aspect of the invention, the degassing system can have a dialysate passage exposed to a first side of a degassing membrane having a permeability coefficient of carbon dioxide greater than the permeability coefficient of oxygen and/or nitrogen. The membrane can be positioned in the degassing vessel to contact a dialysate containing dissolved carbon dioxide. The degassing vessel can have a shell side of the degassing vessel exposed to a second side of the degassing membrane for removing gas, and a vacuum pump connected to the shell side of the degassing vessel to create a low pressure vacuum on the second side of the degassing membrane.

In any embodiment of the first aspect of the invention, degassing system can have a membrane that has a permeability coefficient of carbon dioxide that is any one of about 2.0, 2.5, 3.0, 3.5, 4.0, 4.5 or 5.0 times greater than the permeability coefficient of oxygen and/or the permeability coefficient of carbon dioxide is any one of about 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, or 11.0 times greater than the permeability coefficient of nitrogen.

In any embodiment of the first aspect of the invention, the degassing system can have a degassing membrane constructed from non-porous silicone or poly(dimethylsiloxane).

In any embodiment of the first aspect of the invention, the degassing system can have a degassing membrane compatible with temperatures of at least 80° C.

In any embodiment of the first aspect of the invention, the degassing system can have a degassing membrane compatible with a 2% citric acid solution and/or the membrane is compatible with bleach.

In any embodiment of the first aspect of the invention, the vacuum pump can be any of a gear pump, peristaltic pump, diaphragm pump or impeller pump.

In any embodiment of the first aspect of the invention, the degassing vessel can comprise a fluid inlet and a fluid outlet, wherein dialysate flows into the degassing vessel through the fluid inlet and exits the degassing vessel through the fluid outlet.

In any embodiment of the first aspect of the invention, the fluid inlet can be at a lower elevation than the fluid outlet, such that dialysate travels vertically upward through the degassing vessel. In any embodiment of the first aspect of the invention, the fluid inlet can be at a higher elevation than the fluid outlet, such that dialysate travels vertically upward through the degassing vessel.

In any embodiment of the first aspect of the invention, the degassing membrane can have a permeability coefficient of carbon dioxide that is greater than the permeability coefficient of nitrogen and/or oxygen.

In any embodiment of the first aspect of the invention, the degassing membrane can have a surface area of between any of 1.0-3.5 $m^2$, 1.2-2.0 $m^2$, 1.8-2.5 $m^2$, or 2.0-3.0 $m^2$.

In any embodiment of the first aspect of the invention, the degassing membrane can be compatible with temperatures of at least 80° C. In any embodiment of the first aspect of the invention, the degassing membrane can be compatible with a 2% citric acid solution. In any embodiment of the first aspect of the invention, the degassing membrane can be compatible with bleach. In any embodiment of the first aspect of the invention, the degassing membrane can be placed within a degassing module.

In any embodiment of the first aspect of the invention, the degassing membrane can be positioned in a degassing vessel. In any embodiment of the first aspect of the invention, the degassing vessel can comprise a dialysate passage of the vessel exposed to a first side of the degassing membrane for contacting a dialysate containing dissolved carbon dioxide; a shell side of the degassing vessel exposed to a second side of the degassing membrane for removing gas; and a vacuum pump connected to the shell side of the degassing vessel to create a vacuum on the second side of the degassing membrane.

In any embodiment of the first aspect of the invention, the degassing vessel can comprise one or more sensors positioned in the dialysate passage of the degassing vessel wherein the one or more sensors can monitor the fluid level in the degassing vessel and adjust the flow rate of dialysate entering the degassing vessel in order to maintain a predetermined fluid level in the degassing vessel.

Any of the features described as part of the first aspect of the invention can be included in the first aspect of the invention either alone or in combination.

The second aspect of the invention is directed towards a method. In any embodiment of the second aspect of the invention, the method can comprise contacting a solution containing dissolved carbon dioxide with a first side of a degassing membrane in the degasser, wherein the concentration of a gas on the first side of the degassing membrane is higher than the partial pressure of the gas on a second side of the degassing membrane opposite to the first side, and wherein the degassing membrane has a permeability coefficient for carbon dioxide that is greater than the permeability coefficient for nitrogen and/or oxygen; the method can comprise controlling the gas pressure on the second side of the degassing membrane to control the pressure of $CO_2$ at an outlet of the degasser.

In any embodiment of the second aspect of the invention, the degassing membrane can have a permeability coefficient of carbon dioxide that is any one of about 2.0, 2.5, 3.0, 3.5, 4.0, 4.5 or 5.0 times greater than the permeability coefficient of oxygen and/or the permeability coefficient of carbon dioxide can be any one of about 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, or 11.0 times greater than the permeability coefficient of nitrogen.

In any embodiment of the second aspect of the invention, the pressure on the second side of the degassing membrane can be controlled between a predetermined limit. In any embodiment, the limits can be between 140 and 190 mmHg.

In any embodiment of the second aspect of the invention, the rate of flow of the dialysate that contacts the degassing membrane can be between any one of 50 and 800 mL/min, 150 and 750 mL/min, 250 and 375 mL/min, 75 and 200 mL/min, 150 and 300 mL/min, 250 and 500 mL/min, or 400 and 800 mL/min. In any embodiment of the second aspect of the invention, the flow rate of the dialysate that contacts the degassing membrane can be between 50 and 600 mL/min.

In any embodiment of the second aspect of the invention, the method can be used for degassing a dialysis fluid. In any embodiment of the second aspect of the invention, the dialysis fluid can be an ultrafiltrate. In any embodiment of the second aspect of the invention, the dialysis fluid can be a dialysate. In any embodiment of the second aspect of the invention, the method can be used for degassing blood to be returned to a patient.

In any embodiment of the second aspect of the invention, the degasser can be located in a flow path parallel to a dialysate flow path.

In any embodiment of the second aspect of the invention, the degasser can be located in a dialysate flow path.

Any of the features described as part of the second aspect of the invention can be included in the second aspect of the invention either alone or in combination.

DETAILED DESCRIPTION OF THE INVENTION

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

The term "cartridge" refers to any container designed to contain a powder, fluid, or gas made for ready connection to a device or mechanism. The container can have one or more compartments. Instead of compartments, the container can also be comprised of a system of two or more modules connected together to form the cartridge wherein the two or more modules once formed can be connected to a device or mechanism.

The term "comprising" includes, but is not limited to, whatever follows the word "comprising." Thus, use of the term indicates that the listed elements are required or mandatory but that other elements are optional and may or may not be present.

The term "connectable" refers to being able to be joined together for purposes including but not limited to maintaining a position, allowing a flow of fluid, performing a measurement, transmitting power, and transmitting electrical signals. The term "connectable" can refer to being able to be joined together temporarily or permanently.

A "connector" and "for connection" as used herein describes the concept of forming a fluid connection between two components wherein fluid or gas can flow from one component, through a connector or a component for connection, to another component. It will be understood that the connector provides for a fluid connection in its broadest sense and can include any type of tubing, fluid or gas passageway, or conduit between any one or more components of the invention.

The term "consisting of" includes and is limited to whatever follows the phrase "consisting of." Thus, the phrase indicates that the limited elements are required or mandatory and that no other elements may be present. The term "consisting essentially of" includes whatever follows the term "consisting essentially of" and additional elements, structures, acts or features that do not affect the basic operation of the apparatus, structure or method described.

A "control system" consists of combinations of components that act together to maintain a system to a desired set of performance specifications. The control system can use processors, memory and computer components configured to interoperate to maintain the desired performance specifications. The control system can also include fluid or gas control components, and solute control components as known within the art to maintain the performance specifications.

A "controller," "control unit," "processor," or "microprocessor" is a device which monitors and affects the operational conditions of a given system. The operational conditions are typically referred to as output variables of the system wherein the output variables can be affected by adjusting certain input variables.

A "degasser" is a component that is capable of removing dissolved and undissolved gasses from fluids. The term "degasser" can encompass a degassing vessel, and a fluid pump and a vacuum pump connected to the degassing vessel and working in concert to create a vacuum in the fluid flowing through the degassing vessel and to evacuate gas from the degassing vessel.

A "degassing membrane" is a semi-permeable membrane having a permeability coefficient selective to a particular gas such that specific gases may be removed from dialysate with particularity. The membrane may be constructed of silicone or other materials known in the art having the desired permeability coefficient for the targeted gas to be removed from the dialysate.

A "degassing vessel" is a component of a degasser, and can be any structure having an inlet through which dialysate enters the vessel, a first outlet through which gas removed from the dialysate may pass, and a second outlet through which dialysate can exit the vessel once gas has been removed from the dialysate.

"Dialysate" is the fluid that passes through the dialyzer on the side of the dialysis membrane that is opposite to the fluid (e.g. blood) that is being dialyzed.

The term "dialysate flow loop," "dialysate flow path" or "dialysate conduit flow path" refers to any portion of a fluid pathway that conveys a dialysate and is configured to form at least part of a fluid circuit for hemodialysis, hemofiltration, hemodiafiltration or ultrafiltration.

The term "dialysate passage" refers to a portion of a degassing vessel through which the dialysate is made to flow.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

The terms "dialysis membrane," "hemodialysis membrane," "hemofiltration membrane," "hemodiafiltration membrane," "ultrafiltration membrane," can generally be referred to as a "membrane," or can refer to a semi-permeable barrier selective to allow diffusion and/or convection of solutes between blood and dialysate, or blood and filtrate, of a specific range of molecular weights in either direction through the barrier that separates blood and dialysate, or blood and filtrate, while allowing diffusive and/or convective transfer between the blood on one side of the membrane and the dialysate or filtrate circuit on the other side of the membrane.

The term "dialyzer" refers to a cartridge or container with two flow paths separated by semi-permeable membranes. One flow path is for blood and one flow path is for dialysate. The membranes can be in the form of hollow fibers, flat sheets, or spiral wound or other conventional forms known to those of skill in the art. Membranes can be selected from the following materials of polysulfone, polyethersulfone, poly(methyl methacrylate), modified cellulose, or other materials known to those skilled in the art.

"Flow" refers to the movement of a fluid or gas.

The term "flow loop" refers to a grouping of components that may guide the movement of a fluid, convey the fluid, exchange energy with the fluid, modify the composition of the fluid, measure a characteristic of the fluid and/or detect the fluid. A flow loop comprises a route or a collection of routes for a fluid to move within. Within a flow loop there may be more than one route that a volume of fluid can follow to move from one position to another position. A fluid volume may move through a flow loop such that the fluid volume recirculates, or passes the same position more than once as the fluid volume moves through a flow loop. A flow loop may operate to cause fluid volume ingress to and fluid volume egress from the flow loop. The terms "flow loop" and "flow path" often may be used interchangeably.

A "flow sensing apparatus" or "flow measuring apparatus" is an apparatus capable of measuring the flow of fluid or gas within a specific area.

A "fluid" is a liquid substance optionally having a combination of gas and liquid phases in the fluid. Notably, a liquid, as used herein, can therefore also have a mixture of gas and liquid phases of matter.

The term "fluidly connectable" refers to the ability of providing for the passage of fluid or gas from one point to another point. The two points can be within or between any one or more of compartments, modules, systems, components, and rechargers, all of any type.

A "fluid pump" is a pump used to move fluid throughout a system. In any embodiment, the fluid pump can create low pressure in the degassing vessel such that fluid is drawn into the degassing vessel. In any embodiment, the fluid pump can be used together with a degas restrictor. The fluid pump can work in concert with a vacuum pump to create a low pressure environment within the degassing vessel such that gas is separated from the fluid.

A "gas" is a state of matter, as opposed to liquid, solid or plasma. A gas may be comprised of elemental molecules made from one type of atom (e.g., oxygen, nitrogen), and may comprise compound molecules made from a variety of atoms (e.g., carbon dioxide). Gas may be dissolved or undissolved in a fluid, such as dialysate. At higher pressures, a greater amount of gas will remain dissolved in fluid; however, as the fluid is subjected to lower pressures, the gas will precipitate out of the fluid. In the present invention, the phrase "any other gas" refers to any gas that is not carbon dioxide that may be found in dialysate or any other fluid used in dialysis, such as nitrogen and oxygen.

The term "hydrophobic membrane" refers to a semipermeable porous material that may allow gas phases of matter to pass through the membrane, but which substantially resists the flow of water through the membrane due to the surface interaction between the water and the hydrophobic material of the membrane.

The terms "pathway," "conveyance pathway," "fluid flow path," and "flow path" refer to the route through which a fluid or gas, such as dialysate or blood travels.

A "patient" or "subject" is a member of any animal species, preferably a mammalian species, optionally a human. The subject can be an apparently healthy individual, an individual suffering from a disease, or an individual being treated for a disease.

The term "peristaltic pump" refers to a pump that operates by compression of a flexible conduit or tube through which the fluid to be pumped passes.

The term "permeability coefficient" is the rate of gas permeation per unit area, per unit transmembrane driving force, per unit membrane thickness of a solid, such as a semi-permeable membrane, to a particular permeate (such as a liquid, gas or vapor). For example, a silicone membrane may have a permeability coefficient of 36,000 Barrers to $H_2O$, a permeability coefficient of 280 Barrers to $N_2$, a permeability coefficient of 3,250 Barrers to $CO_2$, and a permeability coefficient of 600 Barrers to $O_2$. The unit of measure, a Barrer, is equal to $10^{-11}$ $cm^3$ (STP)/$cm^2$ sec mmHg.

"Polydimethylsiloxane" or "PDMS" is a silicon-based organic polymer material, and is used in certain embodiments of the present invention to construct a semi-permeable membrane. The material is selected for its particular permeability coefficient of carbon dioxide, which is greater than the permeability coefficient of other gases such as nitrogen or oxygen.

The term "pulsatile pump" refers to a pump wherein the pumped fluid undergoes periodic variation in velocity and/or pressure.

The term "pump" refers to any device that causes the movement of fluids or gases by the application of suction or pressure.

The terms "pump rate" and "volumetric pumping rate" refer to the volume of fluid that a pump conveys per unit of time.

A "sensor" is a component capable of determining the states of one or more variables in a system.

"Shell side" refers to the portion of a degassing vessel on the opposite side of the semi-permeable membrane from the dialysate passage.

"Sorbent cartridge" refers to a cartridge that can contain one or more sorbent materials. The cartridge can be connected to a dialysis flow path. The sorbent materials in the sorbent cartridge are used for removing specific solutes from solution, such as urea. The sorbent cartridge can have a single compartmental design wherein all sorbent materials necessary for performing dialysis are contained within the single compartment. Alternatively, the sorbent cartridge can have a modular design wherein the sorbent materials are dispersed across at least two different modules, which can be connected to form a unitary body. Once the at least two modules are connected together, the connected modules can be referred to as a sorbent cartridge, which can be fitted to a device or mechanism. It will be understood that when a single module contains all the sorbent materials necessary for performing dialysis, the single module can be referred to as a sorbent cartridge.

"Spent dialysate" is a dialysate contacted with blood through a dialysis membrane and contains one or more impurity, or waste species, or waste substance, such as urea.

The term "ultrafiltrate" refers to fluid that is removed from a subject by convection through a permeable membrane during hemodialysis, hemofiltration, hemodiafiltration, or peritoneal dialysis. The term "ultrafiltrate," as used herein, can also refer to the fluid in a reservoir that collects fluid volume removed from the patient, but such a reservoir may also include fluids or collections of fluids that do not originate from the subject.

The term "ultrafiltration" refers to subjecting a fluid to filtration, where the filtered material is very small; typically, the fluid comprises colloidal, dissolved solutes or very fine solid materials, and the filter is a microporous, nanoporous, or semi-permeable medium. A typical medium is a membrane. During ultrafiltration, a "filtrate" or "ultrafiltrate" that passes through the filter medium is separated from a feed fluid. In certain instances, the use of the term "filtrate" can refer to the fluid generated during hemofiltration. In general, when transport across a membrane is predominantly diffusive as a result of a concentration driving force, the process is described herein as dialysis. When transport is primarily convective as a result of bulk flow across the membrane induced by a pressure driving force, the process is ultrafiltration or hemofiltration depending on the need for substitution solution as the membrane passes small solutes but rejects macromolecules. The term "ultrafiltration" can also refer to the fluid removal from blood during a dialysis or a hemofiltration process. That is, ultrafiltration refers to the process of passing fluid through a selective membrane, such as a dialysis or hemofiltration membrane, in dialysis, hemodiafiltration, or a filtration process.

The term "undissolved gases" refers to gases that are not part of a solution, including free gases or bubbles. By contrast, "dissolved gases" include gases dissolved in a fluid such as water or dialysate.

A "vacuum pump" is a pump used to create negative pressure in a degassing vessel, and remove gas from the vessel.

A "valve" is a device capable of directing the flow of fluid or gas by opening, closing or obstructing one or more pathways to allow the fluid or gas to travel in a particular path. One or more valves configured to accomplish a desired flow can be configured into a "valve assembly."

The term "vent" as referred to in relationship to a gas, refers to a means for permitting the escape of a gas from a defined portion of the system, such as, for example, would be found in the degassing module.

Degassing Membrane

The pH of a bicarbonate dialysate can be determined by both the concentration of bicarbonate and the concentration of dissolved carbon dioxide. The bicarbonate concentration of dialysate can generally be controlled within a desired range according to the dialysis prescription. If a bicarbonate dialysate preparation system produces carbon dioxide, then the concentration of dissolved carbon dioxide in the prepared dialysate can be controlled within a corresponding range to maintain dialysate pH within a desired range.

Carbon dioxide can be transferred across a dialysis membrane by the concentration gradient between the dialysate and the blood of the patient receiving treatment. If the dialysate concentration of carbon dioxide is low, carbon dioxide will be transferred from the blood of the patient to the dialysate and the respiration of the patient may be undesirably depressed. If the concentration of carbon dioxide is high, carbon dioxide can be transferred from the dialysate to the blood of the patient and the patient's respiratory system may be undesirably stressed. Carbon dioxide is generated by the breakdown of urea present in spent dialysate into ammonium ions and carbon dioxide by urease present in the sorbent cartridge. Hence, a large amount of carbon dioxide can be present in dialysate as the dialysate leaves the sorbent cartridge. Removal of carbon dioxide, and control of carbon dioxide levels, is an important function of a degasser. When a gas comes in contact with a liquid, either directly or through a membrane, the concentration of that gas in the liquid, expressed as a partial pressure, will be in equilibrium with the gas when its partial pressure in the liquid is equal to its partial pressure in the gas.

Figure 1:
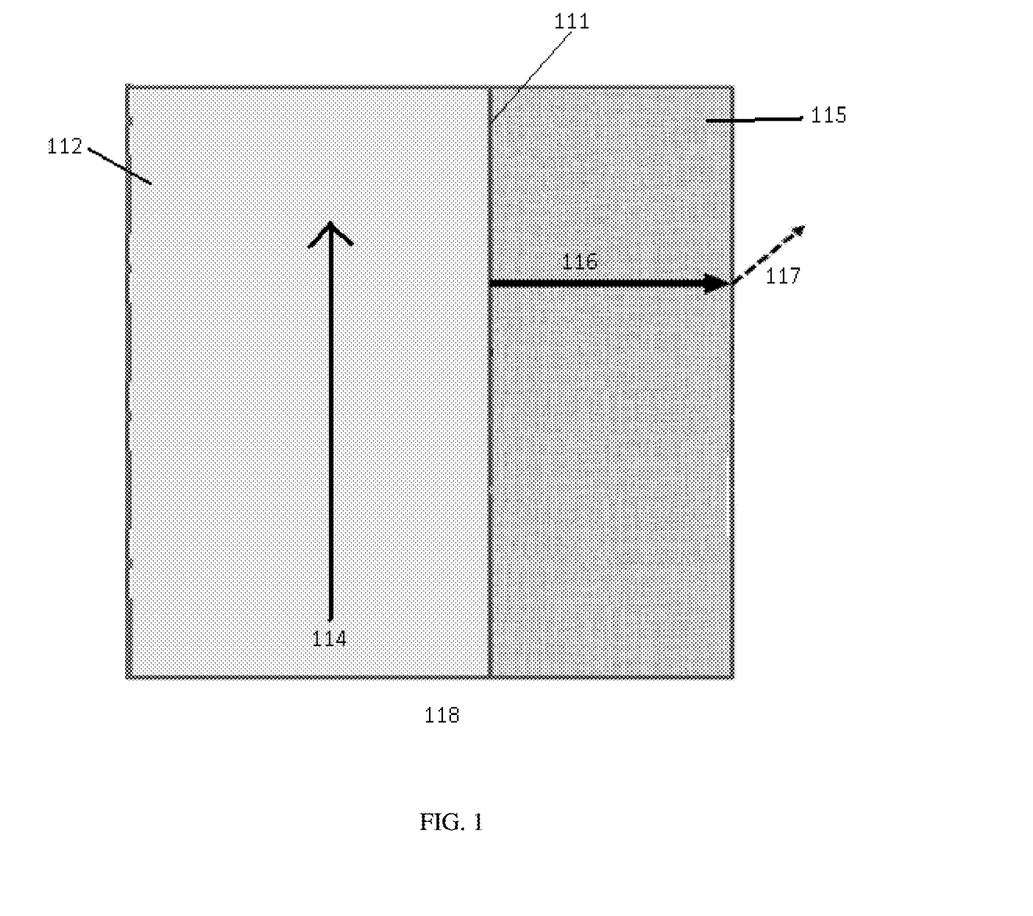
FIG. 1 shows a schematic of a cross-section of a degasser with a degassing membrane.

The degassing system of the first and second aspects of the invention has a membrane having a permeability coefficient of carbon dioxide that is greater than the permeability coefficient of oxygen and nitrogen. The degassing membrane is positioned in a degasser for use in a sorbent dialysis system. FIG. 1 shows a schematic of a cross section of a degassing vessel 118. The dialysate can travel through the dialysate passage 112, represented by arrow 114. As the dialysate travels through the dialysate passage 112, the dialysate contacts degassing membrane 111. The pressure on the shell side 115 of the degassing membrane 111 is controlled by a vacuum pump attached to the degassing vessel (not shown). The low pressure environment created on the shell side of the membrane by the vacuum pump can limit the concentration of gas molecules contained on the shell side of the membrane, such that gases will travel from the liquid, through the membrane to the shell side of the membrane where will be exhausted by the vacuum pump. The gases can permeate the membrane 111 and enter the shell side 115 of the membrane 111, as represented by arrow 116. The dialysate remains in the dialysate passage 112 and continues through the degasser and around the dialysate circuit (not shown). The gases can leave the degassing vessel 118 through the vacuum pump (not shown) as represented by arrow 117.

Figure 2:
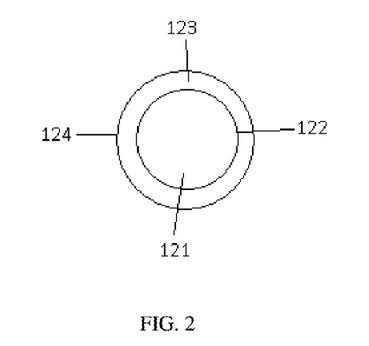
FIG. 2 is a top view of a degasser and degassing membrane.

FIG. 2 shows a top view of a degassing vessel using a membrane 122. The center of the degassing vessel is the dialysate flow passage 121. The dialysate will travel through the degassing vessel in the dialysate flow passage 121. The dialysate contacts the degassing membrane 122 as it travels in the dialysate passage 121. A fluid pump (not shown) is applied to the dialysate flow passage 121 of the degassing membrane 122 to pump the dialysate into the degassing vessel. A vacuum source, such as a pump (not shown) is simultaneously applied to the degassing vessel on the opposite side of the degassing membrane 122 to create remove gas to create an environment having a gas partial pressure in the shell area 123 lower than the partial pressure concentration in the liquid in the dialysate flow passage 121, such that gases dissolved in the dialysate pass through the degassing membrane 122 to the shell area 123, thus reducing the concentration of dissolved gas in the dialysate flow passage 121. The gases can then be removed through the vacuum pump (not shown).

The degassing membrane of the first and second aspects of the invention may be formed of a silicone rubber, which forms a gas permeable membrane across which gases move by diffusion. The rate of gas diffusion is proportional to the product of the solubility of the gas and the rate of diffusion of the dissolved gas in silicone. The silicone rubber membrane can comprise hollow silicone fibers, which may be filled with fluid. One particular type of degassing membrane can be a poly(dimethylsiloxane) membrane (PDMS). PDMS can be selected because silicone fibers are highly permeable to carbon dioxide and water vapor, but are less permeable to other gases, such as oxygen and nitrogen. In any embodiment of the first and second aspects of the invention, the silicone membrane can be non-porous. As opposed to porous hydrophobic membranes, the non-porous membrane of the first and second aspects of the invention can be less permeable to oxygen and nitrogen gas.

As opposed to the non-porous degassing membrane of the first and second aspects of the invention, porous degassing membranes can be roughly equally permeable to carbon dioxide, water vapor, oxygen and nitrogen gases. As a result, with porous degassing membranes, the amount of oxygen and nitrogen removed from the dialysate as the dialysate contacts the degassing membrane will be nearly equal to the amount of carbon dioxide removed. In order to achieve a large degree of removal of carbon dioxide, therefore, large amounts of nitrogen and oxygen will also be removed. Removing less oxygen and nitrogen allows for use of smaller vacuum and fluid pumps, due to a decreased mass flow as compared to degassers using membranes that are highly permeable to oxygen and nitrogen. Smaller vacuum and fluid pumps allow for a smaller and lighter weight dialysis system, thereby increasing portability.

The gas permeability coefficients of the silicone membrane for gases commonly present in dialysate are shown in Table 1. In any embodiment of the first and second aspects of the invention, the permeability coefficient of $CO_2$ is greater than that of $O_2$ or $N_2$. One skilled in the art will understand that other materials can be used as the degassing membrane wherein the permeability coefficient is greater for $CO_2$ than for $O_2$ or $N_2$. In any embodiment of the first and second aspects of the invention, the permeability coefficient for $CO_2$ can be any of 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, or 11.0 times greater than the permeability coefficient of $O_2$ or $N_2$. As is shown in Table 1, in any embodiment of the first and second aspects of the invention, the permeability coefficient of water vapor can be significantly higher than that of $CO_2$, $N_2$, or $O_2$, such as with a PDMS membrane wherein water vapor has a permeability coefficient that is about ten times as high as carbon dioxide. In any such embodiments of the first and second aspects of the invention, water vapor can cross the degassing membrane and be exhausted by the vacuum pump as explained herein.

TABLE 1

| Gas | Formula | Silicone Permeability Coefficient (Barrers) |
|---|---|---|
| Water | $H_2O$ | 36,000 |
| Carbon dioxide | $CO_2$ | 3,250 |
| Oxygen | $O_2$ | 600 |
| Nitrogen | $N_2$ | 280 |

1 Barrer = 10–10 cm3 (STP) · cm/cm2 · s · cm-Hg

The membrane wall of the of the first and second aspects of the invention can ideally have a large enough surface area to effectively allow gas concentration in the dialysate to come into equilibrium with the gas partial pressure on the shell side before the dialysate passes out of the degasser. A smaller surface area will result in less efficient removal of dissolved gases, but may allow for a smaller degasser, thereby allowing for greater portability. A larger surface area may be more efficient in removal of gas, but would increase weight and size of the degasser. Either embodiment is contemplated by the first and second aspects of the invention. In any embodiment of the first and second aspects of the invention, the membrane can have a surface area of 2.1 m². In any embodiment of the first and second aspects of the invention, the membrane can have a larger or smaller surface area. In any embodiment of the first and second aspects of the invention, the surface area of the membrane can be between any of 1.0-3.5 m², 1.2-2.0 m², 1.8-2.5 m², or 2.0-3.0 m².

The degassing membrane of the first and second aspects of the invention, in addition to having a high permeability to carbon dioxide and a low permeability to nitrogen and oxygen, must be able to withstand the disinfection procedure. Disinfection of the dialysis system can include heating the fluid in the dialysate flow loop to temperatures at or above 80° C. The disinfection process may also include washing the dialysis system with about 2% citric acid and bleach.

As illustrated in FIG. 1, the pressure that will exist for each gas on the shell side 115 of the degassing membrane 111 is a function of the low pressure environment on the shell side 115 of the membrane 111 created by a vacuum pump (not shown), the concentration of the gas in the liquid side of the membrane 112, and the permeability coefficient of the membrane 111. Because of the lower permeability for $N_2$ and $O_2$, as shown in Table 1, the relative proportions of oxygen and nitrogen removed from the dialysate will be much less than the relative proportions of carbon dioxide and water vapor removed when a vacuum is pulled on the shell side 115 of the membrane. If the membrane is sufficiently large, the solution pressures of $H_2O$ and $CO_2$ at the outlet of the degasser will move toward equilibrium with their shell-side partial pressures. The vapor pressure of water at physiological temperature is roughly 45 mmHg. Therefore, the partial pressure of carbon dioxide on the shell side of the membrane can be given by the formula: $pCO_2=pV-45$ mmHg, where $pCO_2$ is the partial pressure of carbon dioxide on the shell side of the membrane and pV is the total pressure on the shell side of the membrane due to the vacuum pump. The lower the total pressure on the shell side of the membrane, therefore, the lower the pressure of carbon dioxide in the shell area 115 will be, and the lower the solution pressure of carbon dioxide will be at the outlet of the degassing vessel. The vacuum pressure can be controlled by the vacuum pump, providing a mechanism for a high degree of control over the amount of carbon dioxide in dialysate solution in accordance with the above equation. The oxygen and nitrogen levels in solution will be largely unchanged due to the low permeability of oxygen and nitrogen to the degassing membrane. Because $N_2$ and $O_2$ diffuse easily across the dialyzer membrane, the concentration of $N_2$ and $O_2$ in spent dialysate will tend to be in the normal physiologic range for human blood and can thus remain at a relatively consistent level in the dialysate passing into the degasser. For these reasons $O_2$ and $N_2$ can tend to be relatively constant and may be less important components of the total pressure on the shell side of the membrane.

Figure 3:
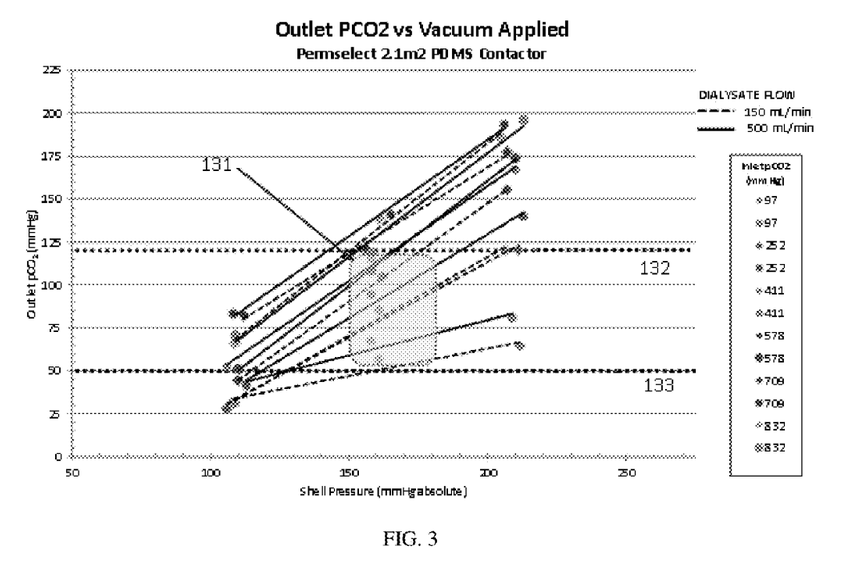
FIG. 3 is a graph showing outlet carbon dioxide concentration as a function of vacuum pressure for an exemplary degassing membrane.

FIG. 3 shows a graph obtained by testing a 2.1 m² PDMS membrane as described above. The graph shows the outlet solution concentration, stated as partial pressure, of carbon dioxide as a function of the pressure on the shell side of the membrane for solutions with a variety of inlet carbon dioxide concentrations, stated as partial pressures. In any embodiment of the first and second aspects of the invention, the ideal outlet solution concentration of carbon dioxide will be between 50 mmHg and 120 mmHg partial pressure, represented by dotted lines 133 and 132, respectively. As is shown by box 131, a vacuum pressure of 165±15 mmHg results in an outlet carbon dioxide concentration between 50 mmHg and 120 mmHg partial pressure for a wide range of inlet carbon dioxide concentrations at either a dialysate flow rate of 150 mL/min or 500 mL/min. In any embodiment of the first and second aspects of the invention, the dialysate flow rate can be between any of 50 and 800 mL/min, 150 and 750 mL/min, 250 and 375 mL/min, 75 and 200 mL/min, 150 and 300 mL/min, 250 and 500 mL/min, or 400 and 800 mL/min. The vacuum pressure can be controlled by the use of a vacuum pump. In any embodiment of the first and second aspects of the invention, the vacuum pressure can be kept higher or lower than 165 mmHg to obtain outlet carbon dioxide concentrations that are higher or lower than 50 mmHg to 120 mmHg partial pressure. In any embodiment of the first and second aspects of the invention, the vacuum pressure can be controlled to result in an outlet carbon dioxide concentration of between any of 10-300 mmHg, 50-120 mmHg, 120-150 mmHg, 150-200 mmHg, or 200-295 mmHg partial pressures.

Figure 4A:
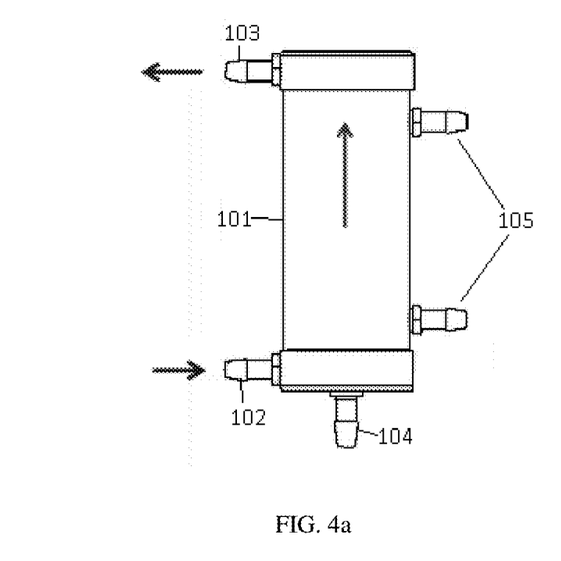
FIG. 4a shows a side view of a degasser with an upward direction of fluid flow.

FIG. 4a shows a non-limiting embodiment of a degasser 101 in accordance with the first and second aspects of the invention. The arrows show the direction of flow of dialysate or other fluids through the degasser 101. Fluid travels into the degasser 101 at inlet 102. In any embodiment of the first and second aspects of the invention, inlet 102 can be at a lower elevation than outlet 103, such that the fluid travels vertically up through the degasser 101 and out of outlet 103. A low pressure environment is generated by a vacuum pump (not shown) attached to the degasser 101 at any of shell-side connectors 104 or 105 to draw the $CO_2$ gas out of the dialysate fluid. The gases can cross a membrane (not shown in FIG. 4a), and exit the degasser 101. The dialysate continues out of the outlet 103 of the degasser in the fluid flow path, as shown in FIG. 2.

Figure 4B:
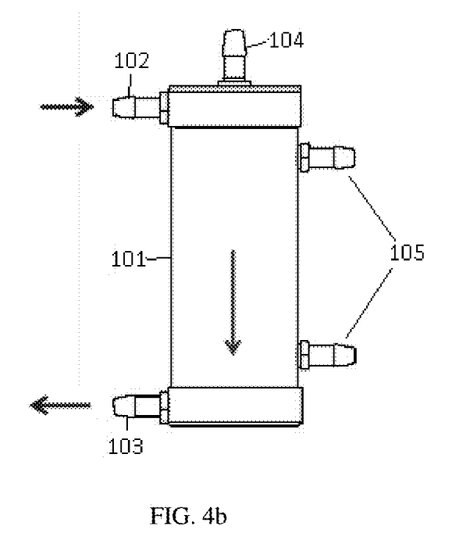
FIG. 4b shows a side view of a degasser with a downward direction of fluid flow.

In any embodiment of the first and second aspects of the invention, flow through the degasser 101 can be in the downward direction, as shown in FIG. 4b, wherein the fluid inlet 102 is at a higher elevation than the fluid outlet 103. Fluid can enter the degasser 101 at inlet 102. It can then travel vertically downward through the degasser 101 and out of outlet 103. A vacuum pump (not shown) can connect to the degasser through connectors 104 and/or 105. The gasses can cross a membrane (not shown) and exit the degasser through ports 104 and/or 105, while the fluid travels out of outlet 103.

Figure 5:
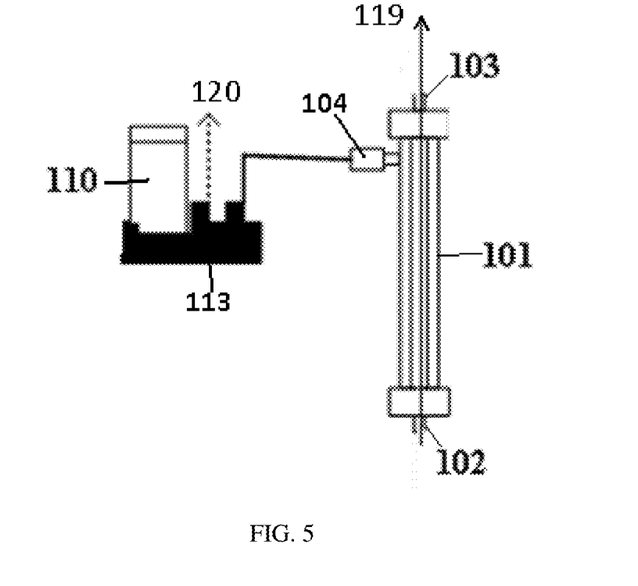
FIG. 5 shows a vacuum gas removal pump pulling dissolved gases across the membrane in the degasser, and venting the gases into the atmosphere.

FIG. 5 shows one embodiment of the arrangement of components for a degasser of the first and second aspects of the invention. In particular, the flow path arrangement utilizes a flow pump (not shown) to move the dialysate or other fluid into the degasser 101 through inlet 102, through the internal fibers of the membrane (not shown) in the degasser 101 as shown by arrow 119, and out of the degasser through outlet 103. At the same time, vacuum pump 110 on vacuum apparatus 113 pulls the dissolved gasses across the membrane (not shown) in the degasser 101, through connector 104, and the gases are subsequently vented into the atmosphere, as shown by arrow 120.

Figure 6:
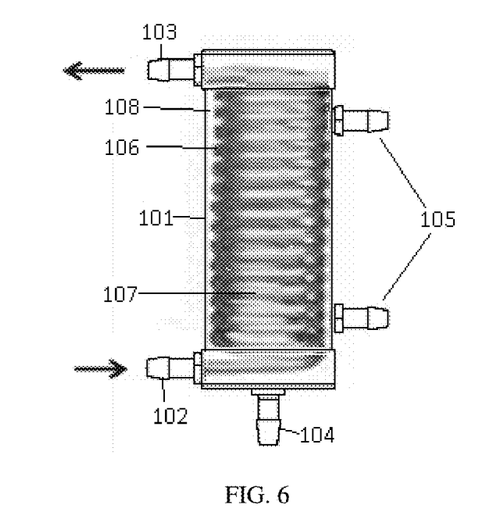
FIG. 6 shows a side view of a degasser with a circuitous dialysate passage.

In any embodiment of the first and second aspects of the invention, flow through the degasser can be controlled to increase the effective surface area of the membrane without increasing the size of the degasser. As shown in FIG. 6, the dialysate passage 107 can be configured so that the dialysate travelling through the degasser 101 takes a circuitous route. This increases the effective length of the dialysate passage 107, and the surface area of the degassing membrane 106, without increasing the overall length of the degasser 101. Dialysate can enter through the degasser inlet 102. The dialysate can then travel through the dialysate passage 107, and out of the degasser outlet 103. Carbon dioxide can pass through the degassing membrane 106 into the shell side of the degasser 108, where the carbon dioxide can exit the degasser 101 through plugs 105. A vacuum pump (not shown) can be attached to the degasser 101 through plug 104 in order to lower the pressure within the degasser 101.

Flow of fluid through the degasser of the first and second aspects of the invention is variable. Control over the flow can be provided by a fluid pump that pumps fluid through the degassing flow loop and the degassing vessel. Under certain operating conditions the flow rate through the degassing flow loop provided by the fluid pump can be less than the flow rate through the main dialysate loop. In any embodiment of the first and second aspects of the invention, the fluid pump can be operated so that flow through the degassing flow loop is significantly greater than that through the main dialysate loop. In any embodiment of the first and second aspects of the invention, the flow through the degassing flow loop can be controlled automatically depending on the amount of carbon dioxide that is to be removed. In any embodiment of the first and second aspects of the invention, the flow of fluid through the degassing flow loop can be any of 2, 3, 4, or 5 times the rate of fluid flow through the main dialysate loop.

The pumps of the degassing module can be of any type known in the art. In any embodiment of the first and second aspects of the invention, all of the pumps in the degassing module can be the same type of pump. In any embodiment of the first and second aspects of the invention, the vacuum pump and the fluid pump can be of different types. In any embodiment of the first and second aspects of the invention, the fluid pump and/or vacuum pump can be gear pumps. In any embodiment of the first and second aspects of the invention, the fluid pump and/or vacuum pump can be peristaltic pumps, diaphragm pumps or impeller pumps. In any embodiment of the first and second aspects of the invention, the fluid pump and/or vacuum pump can also have sensors attached to the pumps to monitor performance of the pump and detect wear. In any embodiment of the first and second aspects of the invention, the pumps must be selected so that they can operate at the low absolute pressure necessary to effectively remove carbon dioxide from the dialysate.

To make use of the dialysis system easier, the valves and pumps may be operated by a programmable controller or computer system that can be programmed to regulate flow through the valves and into and out of the reservoirs. An optical sensor, photocell or other flow sensing apparatus may detect the flow of fluid through any two points in the sorbent cartridge. For example, an optical fluid flow device can be provided for measuring flow wherein the device includes an optical fluid pressure measuring device having sensors positioned in any one of the flow paths between the reservoirs, in the connectors, or in the valves or valve assemblies. In any embodiment of the first and second aspects of the invention, the optical fluid sensors described above can be connected to an interferometer associated with an opto-electronic demodulator which has an output signal representing the differential pressure between the two sensed areas. In any embodiment of the first and second aspects of the invention, a flow sensing apparatus can have a flow-responsive element projecting into a fluid flow path, and a position sensor associated with the element which detects a change in position of the flow-responsive element in response to the fluid flow. The flow-responsive element can be made of a wide variety of materials having the desired properties known to those of ordinary skill in the art.

It will be understood that the degassing membrane of the first and second aspects of the invention can be used to remove carbon dioxide from fluid in any dialysis mode, including hemodialysis, hemofiltration, hemodiafiltration, ultrafiltration or peritoneal dialysis. The degasser can be placed anywhere in a dialysis system, including on the blood side of the dialyzer in order to remove carbon dioxide from the blood that is being returned to the patient. In any embodiment of the first and second aspects of the invention, the degassing system can be used to degas any dialysis fluid. In any embodiment of the first and second aspects of the invention, the dialysis fluid can be an ultrafiltrate or a dialysate, depending on the location of the degasser and the fluid that is directed through the degasser.

The degassing system of the first and second aspects of the invention can be placed anywhere in a dialysis flow path. In any embodiment of the first and second aspects of the invention, the degassing system can be placed in a degassing flow path parallel to the main dialysate flow path. Fluid from the main dialysate flow path can be diverted into the degassing flow path and then be directed back into the main dialysate flow path. In any embodiment of the first and second aspects of the invention, the degassing system can be positioned at a position in the dialysate flow path. This can cause all of the fluid travelling through the dialysate flow path to enter the degassing system, unless the fluid is diverted around the degassing vessel.

It will be apparent to one skilled in the art that various combinations and/or modifications and variations can be made in the dialysis system depending upon the specific needs for operation. Moreover features illustrated or described as being part of an aspect of the invention can be included in the aspect of the invention, either alone or in combination.

We claim:

1. A degassing system, comprising:
   a degassing vessel having a dialysate passage exposed to a first side of a degassing membrane having a permeability coefficient of carbon dioxide greater than the permeability coefficient of oxygen and/or nitrogen;
   the membrane positioned in the degassing vessel to contact a dialysate containing dissolved carbon dioxide;
   a shell side of the degassing vessel exposed to a second side of the degassing membrane for removing gas;
   a vacuum pump connected to the shell side of the degassing vessel to create a low pressure vacuum on the second side of the degassing membrane; and
   a controller regulating a dialysate flow rate through the degassing vessel and a flow rate through a main dialysate flow path.

2. The degassing system of claim 1, wherein the membrane has a permeability coefficient of carbon dioxide that is any one of about 2.0, 2.5, 3.0, 3.5, 4.0, 4.5 or 5.0 times greater than the permeability coefficient of oxygen and/or the permeability coefficient of carbon dioxide is any one of about 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, or 11.0 times greater than the permeability coefficient of nitrogen.

3. The degassing system of claim 1, wherein the membrane is constructed from non-porous silicone or poly(dimethylsiloxane).

4. The degassing system of claim 1, wherein the membrane has a surface area of between any of 1.0-3.5 $m^2$, 1.5-2.0 $m^2$, 2.0-2.5 $m^2$, or 2.5-3.0 $m^2$.

5. The degassing system of claim 1 wherein the membrane is compatible with temperatures of at least 80° C.

6. The degassing system of claim 1 wherein the membrane is compatible with a 2% citric acid solution and/or the membrane is compatible with bleach.

7. The degassing system of claim 1 wherein the vacuum pump is any of a gear pump, peristaltic pump, diaphragm pump or impeller pump.

8. The degassing system of claim 1, wherein the degassing vessel further comprises a fluid inlet and a fluid outlet; wherein dialysate flows into the degassing vessel through the fluid inlet and exits the degassing vessel through the fluid outlet.

9. The degassing system of claim 8, wherein the fluid inlet is at a lower elevation than the fluid outlet, such that dialysate travels vertically upward through the degassing vessel.

10. The degassing system of claim 8, wherein the fluid inlet is at a higher elevation than the fluid outlet, such that dialysate travels vertically downward through the degassing vessel.

11. A method, comprising the steps of:
    contacting a solution containing dissolved carbon dioxide with a first side of a degassing membrane in a degasser, wherein the concentration of a gas on the first side of the degassing membrane is higher than the partial pressure of the gas on a second side of the degassing membrane opposite to the first side, and wherein the degassing membrane has a permeability coefficient for carbon dioxide that is greater than the permeability coefficient for nitrogen and/or oxygen;
    controlling the gas pressure on the second side of the degassing membrane to control the concentration of carbon dioxide at an outlet of the degasser; and
    regulating a solution flow rate through the degasser and a solution flow rate through a main solution flow path.

12. The method of claim 11, wherein the degassing membrane has a permeability coefficient of carbon dioxide that is any one of about 2.0, 2.5, 3.0, 3.5, 4.0, 4.5 or 5.0 times greater than the permeability coefficient of oxygen and/or the permeability coefficient of carbon dioxide is any one of about 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, or 11.0 times greater than the permeability coefficient of nitrogen.

13. The method of claim 11 wherein the pressure on the second side of the degassing membrane is controlled between a predetermined limits.

14. The method of claim 11 wherein the rate of flow of the solution contacting the degassing membrane is between any of 50 and 800 mL/min, 150 and 750 mL/min, 250 and 375 mL/min, 75 and 200 mL/min, 150 and 300 mL/min, 250 and 500 mL/min, or 400 and 800 mL/min.

15. The method of claim 11 used for degassing a dialysis fluid.

16. The method of claim 15 wherein the dialysis fluid is an ultrafiltrate.

17. The method of claim 15 wherein the dialysis fluid is a dialysate.

18. The method of claim 11, wherein the main solution flow path is an extracorporeal flow path, and the method is used for degassing blood to be returned to a patient.

19. The method of claim 11 wherein the degasser is located in a flow path that is parallel to a dialysate flow path.

20. The degassing system of claim 1, further comprising at least one flow sensor in the main dialysate flow path and at least one flow sensor in a flow path through the degassing vessel.

21. The degassing system of claim 1, further comprising a fluid pump wherein the controller controls the flow rate through a degassing flow path provided by the fluid pump to be less than the flow rate through the main dialysate flow path.

22. The degassing system of claim 1, further comprising a fluid pump wherein the controller controls the flow rate through the degassing flow path provided by the fluid pump to be greater than the flow rate through the main dialysate path.

* * * * *